US 6,179,837 B1

(12) United States Patent
Hooven

(10) Patent No.: US 6,179,837 B1
(45) Date of Patent: Jan. 30, 2001

(54) BIPOLAR ELECTROSURGICAL SCISSORS

(75) Inventor: Michael D. Hooven, Cincinnati, OH (US)

(73) Assignee: Enable Medical Corporation, West Chester, OH (US)

( * ) Notice: Under 35 U.S.C. 154(b), the term of this patent shall be extended for 0 days.

(21) Appl. No.: 08/399,421

(22) Filed: Mar. 7, 1995

(51) Int. Cl.[7] .................................................. A61B 18/14
(52) U.S. Cl. .................................. 606/50; 606/48; 606/51
(58) Field of Search ................................ 606/48, 50, 51

(56) References Cited

U.S. PATENT DOCUMENTS

| Re. 29,088 | 12/1976 | Shaw ........................ 128/303.17 |
|---|---|---|
| 659,409 | 10/1900 | Mosher . |
| 1,586,645 | 6/1926 | Bierman . |
| 1,798,902 | 3/1931 | Raney . |
| 2,031,682 | 2/1936 | Wappler et al. ..................... 174/89 |
| 2,433,067 | 12/1947 | Russell . |
| 2,926,232 | 2/1960 | Gard . |
| 3,042,101 | 7/1962 | Spunt . |
| 3,460,539 | 8/1969 | Anhalt . |
| 3,651,811 | 3/1972 | Hildebrandt et al. ........... 128/303.17 |
| 3,685,518 | 8/1972 | Beuerle et al. ................. 128/303.17 |
| 3,730,188 | 5/1973 | Ellman ............................ 128/303.14 |
| 3,768,482 | 10/1973 | Shaw .............................. 128/303.1 |
| 3,826,263 | 7/1974 | Cage et al. ....................... 128/303.1 |
| 3,858,586 | 1/1975 | Lessen ............................. 128/303.1 |
| 3,934,115 | 1/1976 | Peterson ............................... 219/223 |
| 3,970,088 | 7/1976 | Morrison ....................... 128/303.14 |
| 3,987,795 | 10/1976 | Morrison ....................... 128/303.14 |
| 4,003,380 | 1/1977 | Wien .............................. 128/303.17 |
| 4,033,351 | 7/1977 | Hetzel ........................... 128/303.14 |
| 4,043,342 | 8/1977 | Morrison, Jr. ................. 128/303.14 |
| 4,092,986 | 6/1978 | Schneiderman ................ 128/303.14 |
| 4,128,099 | 12/1978 | Bauer ............................. 128/303.17 |
| 4,161,950 | 7/1979 | Doss et al. ..................... 128/303.14 |
| 4,207,896 | 6/1980 | Shaw ................................ 128/303.1 |
| 4,228,800 | 10/1980 | Degler, Jr. et al. ............. 128/303.14 |

(List continued on next page.)

FOREIGN PATENT DOCUMENTS

| 0 572 131 A1 | 1/1993 | (EP) | ............................. A61B/17/39 |
|---|---|---|---|
| 0717 966 A1 | 6/1996 | (EP) | ............................. A61B/17/39 |
| 2 355 521 | 2/1978 | (FR) . | |
| 2 647 683 | 12/1990 | (FR) . | |
| 1 546 624 | 5/1979 | (GB) . | |
| 2 037 167 | 7/1980 | (GB) . | |
| 2 066 104 | 7/1981 | (GB) . | |
| 2 128 881 | 5/1984 | (GB) . | |
| 2 133 290 | 7/1984 | (GB) . | |
| 342619 | 7/1972 | (SU) . | |
| 575103 | 10/1977 | (SU) . | |

OTHER PUBLICATIONS

1979 Brochure entitled, "The Cavitron Bipolar Coagulator," by Cavitron Surgical Systems.
Article entitled, "Combined Biathermy Forceps and Scissors," by D. Lang Stevenson in The Lancet, Oct. 24, 1959.
Article entitled, "Two new laparoscopic instruments: Bipolar sterilizing forceps and uterine manipulator," by Stephen L. Corson, MD, in Association for the Advancement of Medical Instrumentation, Jan.–Feb., 1977 issue.

Primary Examiner—Lee Cohen
(74) Attorney, Agent, or Firm—Cook, Alex, McFarron, Manzo, Cummings & Mehler, Ltd.

(57) ABSTRACT

Bipolar electrosurgical scissors are disclosed having a pair of blades joined for relative movement in a scissor-like action between open and closed positions. At least one of the blades comprises a tissue contacting surface and first and second spaced apart electrodes extending along the surface. Current flow between the first and second electrodes promotes hemostasis in tissue contacting the surface. Preferably, each blade of the scissors includes first and second spaced-apart electrodes.

10 Claims, 8 Drawing Sheets

U.S. PATENT DOCUMENTS

| | | | |
|---|---|---|---|
| 4,232,676 | 11/1980 | Herczog | 128/303.14 |
| 4,248,231 | 2/1981 | Herczog et al. | 128/303.14 |
| 4,271,838 | 6/1981 | Lasner et al. | 128/318 |
| 4,353,371 | 10/1982 | Cosman | 128/303.17 |
| 4,370,980 | 2/1983 | Lottick | 128/303.17 |
| 4,492,231 | 1/1985 | Auth | 128/303.17 |
| 4,590,934 | 5/1986 | Malis et al. | 128/303.14 |
| 4,643,190 | 2/1987 | Heimberger | 128/321 |
| 4,655,216 | 4/1987 | Tischer | 128/303.17 |
| 4,657,017 | 4/1987 | Sorochenko | 128/303.14 |
| 4,669,471 | 6/1987 | Hayashi | 128/321 |
| 4,671,274 | 6/1987 | Sorochenko | 128/303.14 |
| 4,674,498 | 6/1987 | Stasz | 128/303.14 |
| 4,763,669 | 8/1988 | Jaeger | 128/751 |
| 4,785,807 | 11/1988 | Blanch | 128/303.14 |
| 4,819,633 | 4/1989 | Bauer et al. | 128/303.17 |
| 4,848,337 | 7/1989 | Shaw et al. | 128/303.1 |
| 4,850,353 | 7/1989 | Stasz et al. | 128/303.14 |
| 4,887,612 | 12/1989 | Esser et al. | 128/751 |
| 4,905,691 | 3/1990 | Rydell | 606/47 |
| 4,940,468 | 7/1990 | Petillo | 606/170 |
| 4,944,093 | 7/1990 | Falk | 30/251 |
| 4,969,885 | 11/1990 | Farin | 606/38 |
| 4,977,900 | 12/1990 | Fehling et al. | 128/751 |
| 4,985,030 | 1/1991 | Melzer et al. | 606/51 |
| 5,007,908 | 4/1991 | Rydell | 606/47 |
| 5,009,656 | 4/1991 | Reimels | 606/48 |
| 5,035,696 | 7/1991 | Rydell | 606/47 |
| 5,047,026 | 9/1991 | Rydell | 606/48 |
| 5,085,659 | 2/1992 | Rydell | 606/47 |
| 5,108,391 | 4/1992 | Flachenecker et al. | 606/38 |
| 5,147,356 | 9/1992 | Bhatta | 606/37 |
| 5,147,357 | 9/1992 | Rose et al. | 606/49 |
| 5,250,047 | 10/1993 | Rydell | 606/48 |
| 5,258,006 | 11/1993 | Rydell et al. | 606/205 |
| 5,282,799 | 2/1994 | Rydell | 606/48 |
| 5,308,311 | 5/1994 | Eggers et al. | 606/28 |
| 5,312,434 | 5/1994 | Crainich | 606/207 |
| 5,318,564 | 6/1994 | Eggers | 606/47 |
| 5,324,289 | 6/1994 | Eggers | 606/40 |
| 5,330,471 | 7/1994 | Eggers | 606/48 |
| 5,342,359 | 8/1994 | Rydell | 606/51 |
| 5,342,381 | 8/1994 | Tidemand | 606/174 |
| 5,352,222 | 10/1994 | Rydell | 606/37 |
| 5,356,408 | 10/1994 | Rydell | 606/48 |
| 5,391,166 | 2/1995 | Eggers | 606/48 |
| 5,403,312 | 4/1995 | Yates et al. | 606/50 |
| 5,433,463 | * 7/1995 | Stern et al. | 606/51 |
| 5,445,638 | 8/1995 | Rydell et al. | 606/51 |
| 5,456,684 | 10/1995 | Schmidt et al. | 606/41 |
| 5,462,546 | 10/1995 | Rydell | 606/51 |
| 5,496,312 | * 3/1996 | Klicek | 606/51 |
| 5,540,685 | 7/1996 | Parins et al. | 606/51 |

* cited by examiner

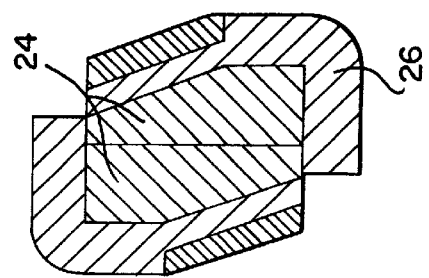
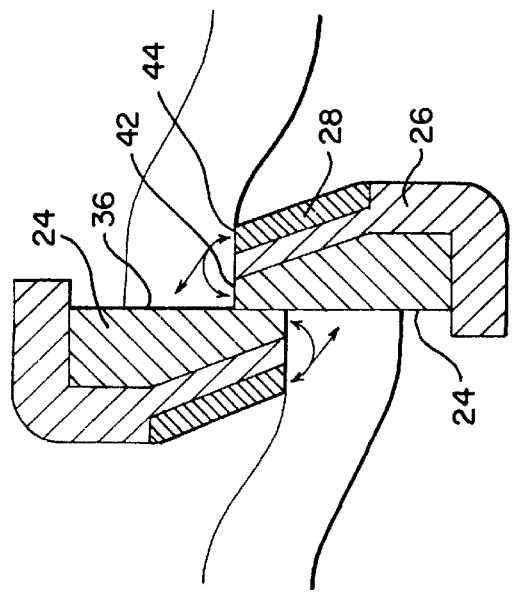
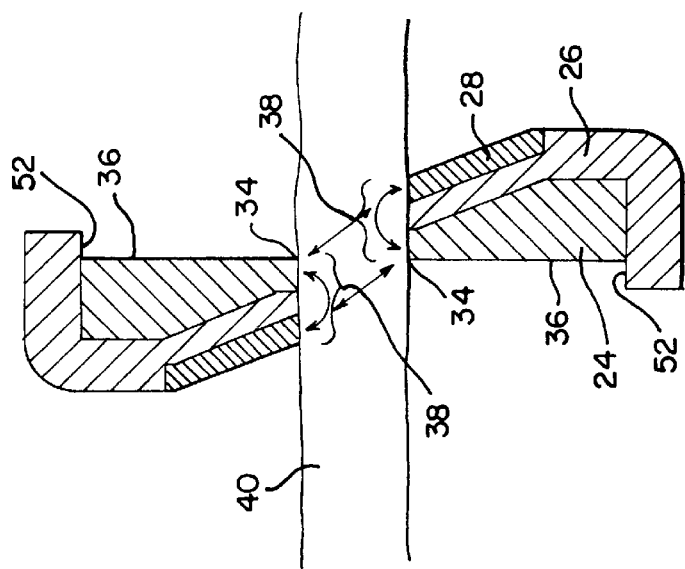

BIPOLAR ELECTROSURGICAL SCISSORS

The present invention relates generally to electrosurgical scissors, and more particularly, to bipolar electrosurgical scissors to assist in hemostasis of tissue as it is cut by the scissors.

BACKGROUND OF THE INVENTION

It is common in many surgical procedures to use surgical scissors for cutting tissue that is vascularized, i.e., contains blood vessels. The resultant bleeding that occurs is not only of concern from the standpoint of blood loss, but the blood may also obscure the surgical field or site. Controlling such bleeding has, in the past, required significant time and attention of the surgeon during many surgical procedures.

In recent years, efforts have been devoted to developing scissors that use radiofrequency ("RF") energy in a manner such that the tissue is heated as it is cut, to promote immediate hemostasis. Early efforts at such electrosurgial scissors used monopolar RF power, where the scissors constituted one electrode, and the patient rested on the other electrode, which was typically in the form of a conductive mat, to complete the circuit. Current flowed generally through the patient between the electrodes due to a voltage applied across the electrodes by an RF power supply.

Monopolar applications, however, had certain drawbacks. Inadvertent contact between the scissors and other tissue could result in unwanted tissue damage. In addition, the flow of current through the body of the patient could take uncertain or unpredictable paths with potential unwanted injury to other tissue. More recently, efforts have been made to develop bipolar electrosurgical scissors to overcome the drawbacks with monopolar scissors. Specifically, efforts have been made to develop scissors in which one blade includes one electrode and the other blade includes the other electrode, so that current flows between the blades as they cut the desired tissue.

Example of recent efforts to develop bipolar scissors are found in U.S. Pat. Nos. 5,324,289 and 5,330,471. These patents disclose bipolar scissors in which one blade of the scissors has one electrode, and the other blade of the scissors has the other electrode, so that current flows between the blades as they come into proximity during cutting. Various embodiments of bipolar scissors are disclosed in these patents, but typically a layer of insulating material is provided on at least one shearing surface of one of the blades, and the hinge pin or fastener which pivotally connects the blades is electrically insulated, so that the electrically active parts of the scissor blades do not contact each other during operation of the instrument. With the construction as shown in these patents, the electrical current flows between the blades at a point just forward of where the shearing surfaces actually touch. The current flow between the blades causes a heating of the tissue and promotes local coagulation and hemostasis during the cutting procedure.

In U.S. Pat. No. 5,352,222, bipolar scissors are shown in which each blade of the scissors is a laminated assembly of a metal shearing surface, a metal blade support and intermediate layer of insulating material. The blade support of one blade acts as one electrode, and the blade support of the other blade acts as the other electrode, so that electrical energy flows between the blade supports as the blades close on the tissue being cut. A short circuit between the shearing surface is prevented by reason of the insulating layer between the metal shearing surface and the blade support. This scissor construction is purported to be more economical to manufacture than the blade structure disclosed in U.S. Pat. Nos. 5,324,289 and 5,330,471. However, because the shearing surface is a separate piece, bonded to the blade support, a particularly high strength and high precision epoxy bonding process is required in the '222 patent so that the shearing surface remains attached to the blade support despite the shearing forces exerted upon it during repeated cutting.

What the above patents have in common, is that each blade forms one of the electrodes attached to a bipolar RF energy source, so that the only current that flows is between the blades as they close. Although the bipolar scissors described in the above-identified patents are believed to be an advance over the earlier monopolar scissors, they typically required the electrically active parts of the blades to be insulated from one another, which tends to complicate the design and materials of the blade actuating mechanism. Accordingly, development work continues to provide bipolar scissors which are easy to use, more economic to make, versatile and/or which are effective in promoting hemostasis during cutting of various tissues, particularly including tissues that are highly vascularized.

SUMMARY OF INVENTION

In accordance with the present invention, tissue cutting apparatus, such as scissors, may be provided in which each cutting blade itself includes two electrodes for connection to a bipolar RF energy power supply. More specifically, the tissue cutting apparatus of the present invention comprises a pair of blades joined for relative movement in a scissor-like action between open and closed positions. Each of the blades has a tissue contacting surface for contacting the tissue therebetween as the blades close during the cutting action. The tissue contacting surface of at least one and preferably both blades includes first and second spaced-apart electrodes which extend along the tissue contacting surface and are connectable to a voltage source, such as a high frequency bipolar RF power supply, for applying a voltage between the electrodes. As a result, current flows between the first and second electrodes of the blade to promote hemostasis in the tissue as the blade is moved into contact with tissue, such as during the cutting action.

In accordance with other aspects of the present invention, the first electrode of each of the blades may also define a shearing surface and a cutting edge of the blade. As in typical surgical scissors, the shearing surfaces of the blades are in a face-to-face relationship, but in accordance with the preferred aspects of the present invention, the first electrodes of each blade are of like polarity, so that there is no short circuiting between the shearing surfaces of the blades. Because the contacting shearing surfaces are of like polarity, there is no need to insulate the blades from one another, and a less complicated and less expensive scissor construction is required than in the prior patents discussed above. In accordance with this aspect of the present invention, the scissor shaft, which extends between the blades and an actuator handle, may itself be a conductor for connecting the first electrode of each blade to one terminal of a voltage source, and a single insulated conductor extending along the shaft may be used to connect the second electrode of each blade to the other terminal of the voltage source. Further, where the first electrode defines the cutting edge and shearing surface and also serves as the main structural element of each blade, relatively little force is exerted on the second electrode during cutting. As a result, a special high strength or high precision bonding process between the first and second electrodes is unnecessary, and less expensive bonding techniques should suffice.

In the above-described embodiment, the first and second electrodes preferably extend along a tissue contacting edge of the scissors, which is in proximity to the cutting edge. Accordingly, the current flow between the first and second electrodes serves to promote hemostasis in close proximity to the cut line, as the scissors are closed in a cutting action.

In accordance with another feature of the present invention, the first and second electrodes of each blade are located so that current not only flows between the first and second electrodes of each blade, but also between the first electrode of one blade and the second electrode of the other blade as the blades are brought into proximity during cutting. The flow of current between electrodes of different blades and electrodes of the same blade enhances coagulation and hemostasis during the cutting action.

In accordance with another aspect of the present invention, the scissors embodying the present invention may be used to promote coagulation during a blunt dissection or similar procedure, where the opening action of the scissors is used to contact or spread tissue. In this embodiment, each scissor blade has first and second spaced electrodes that extend along the rearward edge of the blades to contact tissue and promote coagulation as the blades are opened to spread or open tissue.

These and the many other features of the present invention, are set forth in the following detailed description of the attached drawings.

BRIEF DESCRIPTION OF THE DRAWINGS

FIGS. 4a–4c are vertical cross-sectional views of one embodiment of scissor blades employing the present invention, taken along line 4—4 of FIG. 3, and showing the positions of the blades as they move from an open position in FIG. 4a in contact with the tissue to be cut, to an intermediate position in FIG. 4b just after the tissue is cut, and to a fully closed position in FIG. 4c.

DETAILED DESCRIPTION OF THE DRAWINGS

Figure 1:
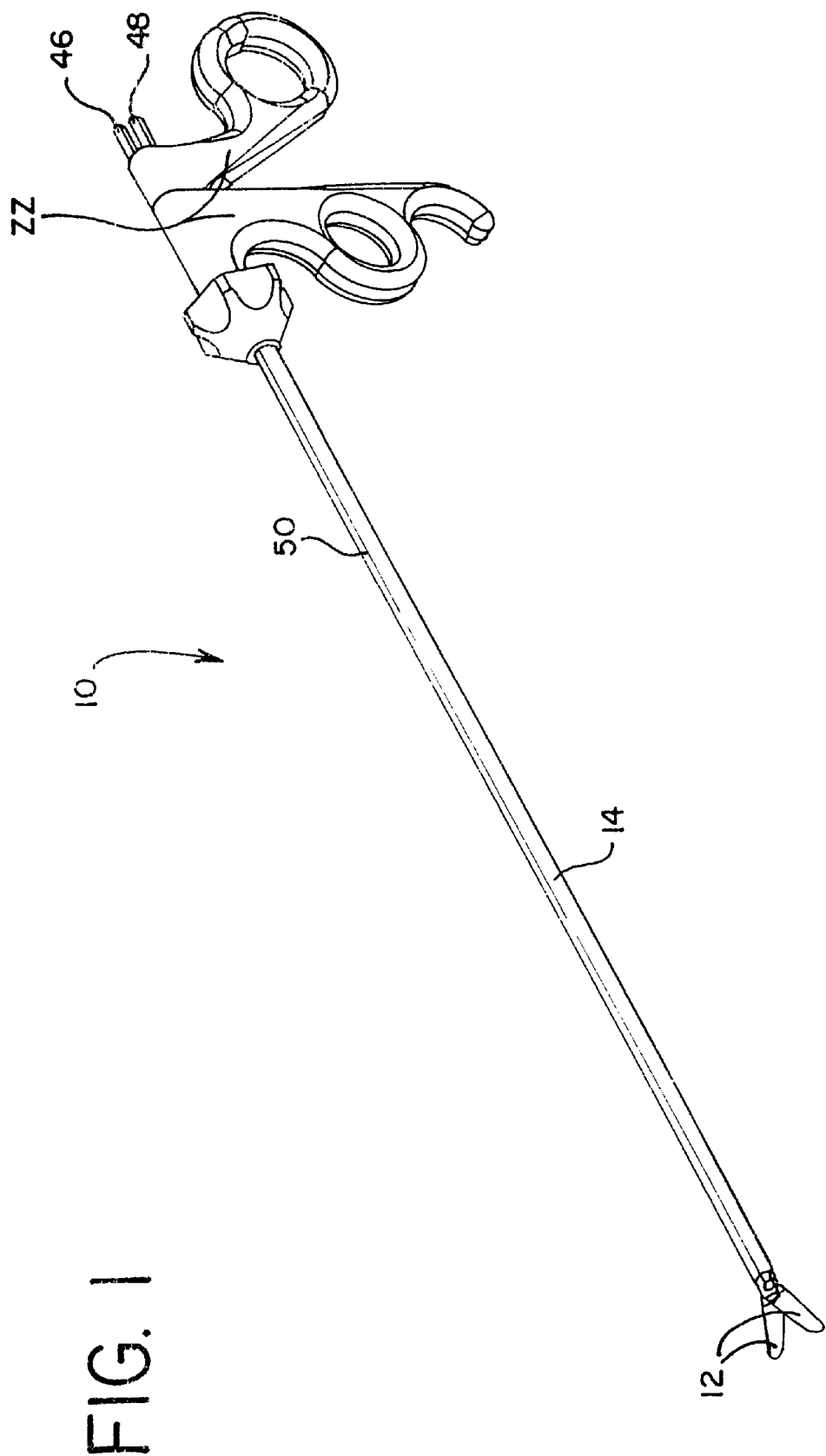
FIG. 1 is a perspective view of electrosurgical scissors embodying the present invention.

Referring to FIG. 1, the present invention is generally embodied in electrosurgical scissors, generally at 10, having a pair of scissor blades 12 joined for pivotal movement between open and closed positions. The present invention is not limited to any particular type or style of surgical scissors, and may be used in essentially any scissors that has a pair of movable blades. The particular scissors 10 shown in FIG. 1 is the type of scissors typically used in so-called minimally invasive surgery, where the scissor blades are inserted into the body cavity of a patient through a small diameter trocar.

Figure 2:
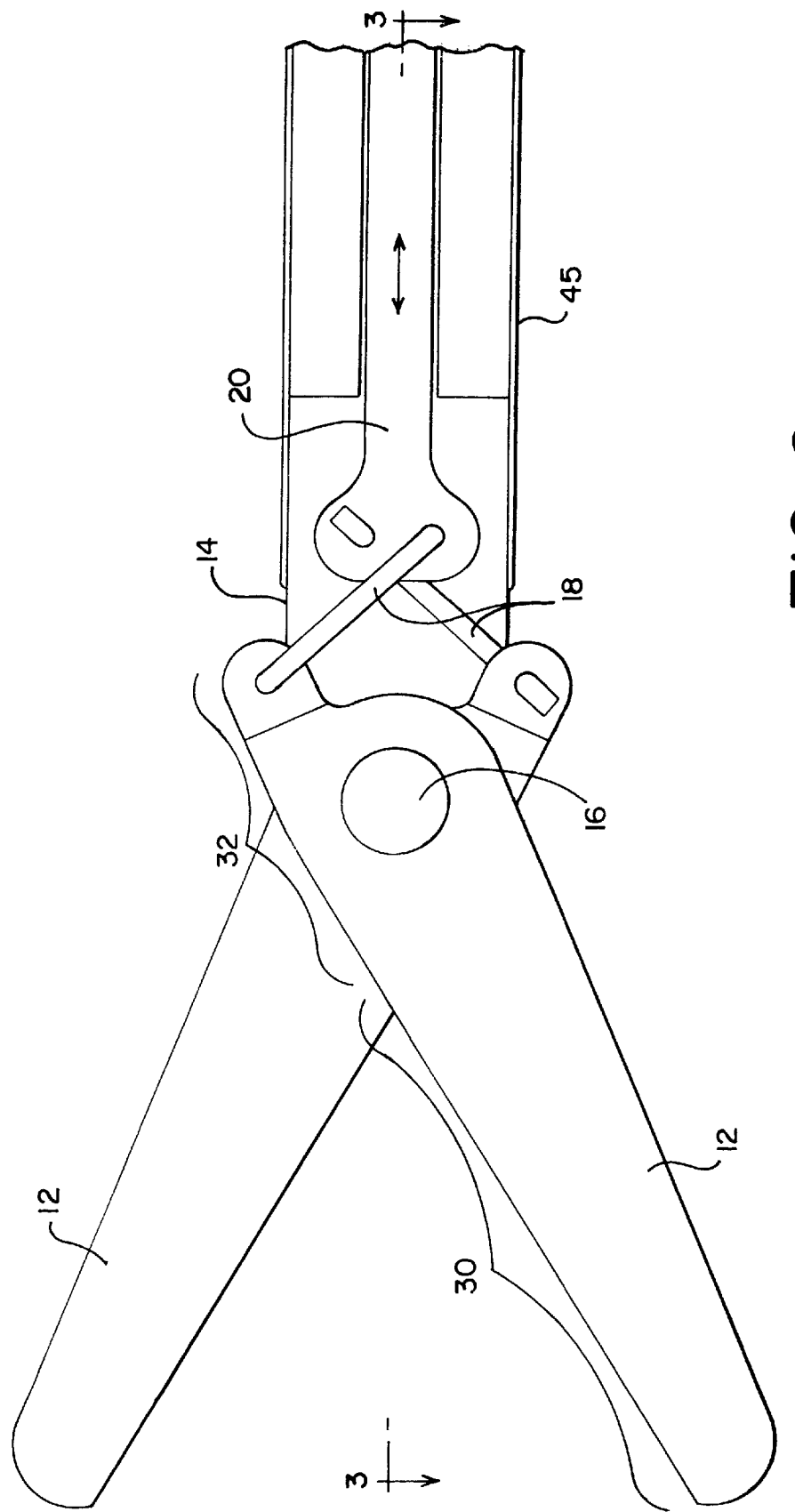
FIG. 2 is a cross-sectional view of the distal end of the electrosurgical scissors of FIG. 1, depicting one means for attaching and moving the blades between open and closed positions, with the blades shown in an open position.
Figure 3:
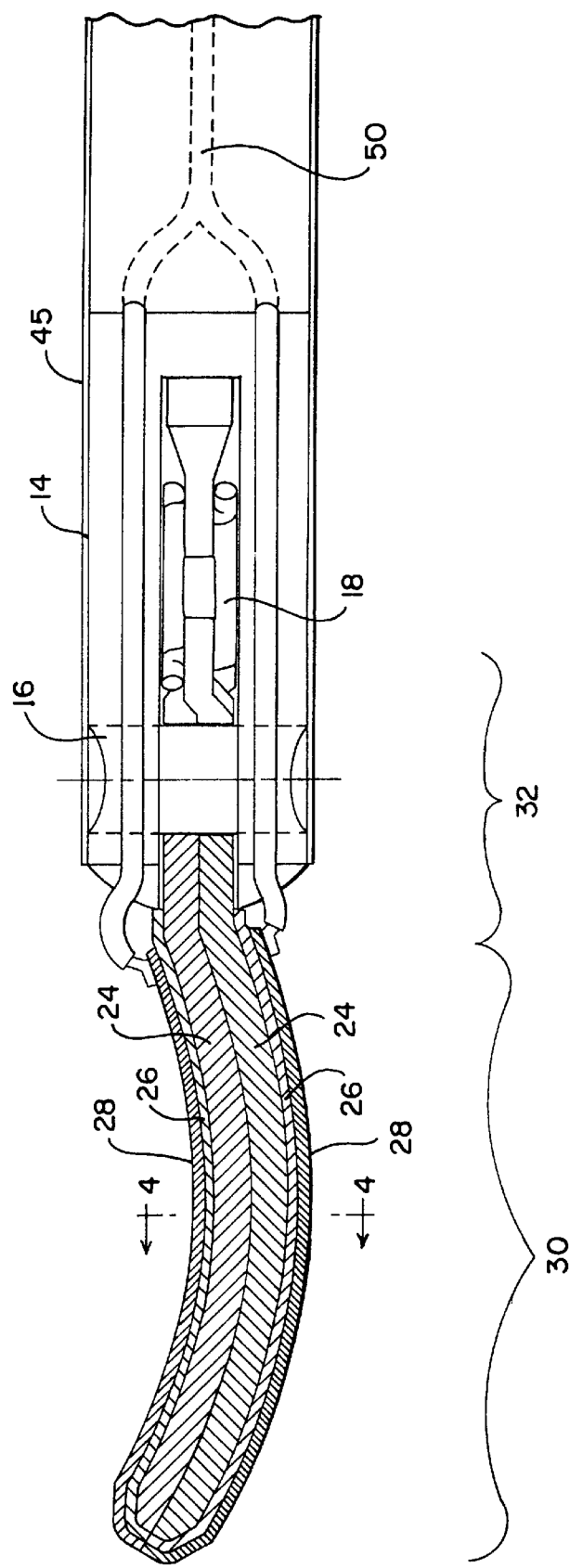
FIG. 3 is a longitudinal cross-sectional view of the distal end of the electrosurgical scissors of FIG. 2, taken along line 3—3 of FIG. 2, with the blades shown in a closed position.

In the scissors 10, the scissor blades are located at the distal of an elongated tubular shaft 14. As shown in FIGS. 2 and 3, the blades 12 are pivotally attached by pivot pin 16, which also attaches the blades to the distal end of shaft 14. A pair of linkages 18 connect the proximal ends of the blades to an actuator rod 20 that extends through the shaft. Axial movement of the actuator rod, which is controlled by handle 22 (FIG. 1) in a standard and well-known fashion, closes or opens the blades.

Alternatively, the proximal ends of the blades 12 may be slotted and the actuator rod 20 connected to a pin that slides within the slots, so that axial movement of the actuator rod opens and closes the blades. Examples of scissors employing a similar but somewhat more complicated structure than necessary in the present invention are described in U.S. Pat. Nos. 5,330,471 and 5,352,222, which are incorporated by reference herein.

In accordance with the present invention, as shown in FIG. 3, and in FIGS. 4–7, at least one blade, and preferably each blade of the scissors includes an inner conductive blade element 24 which defines a first electrode, an intermediate layer of insulative material 26 and an outer conductive blade element 28 which defines a second electrode. The inner blade element 24 includes a distal curved (or straight if desired) blade segment 30, which extends generally from pivot pin 16, and a proximal mounting segment 32 that is typically received within the end of shaft 14 and receives pivot pin 16 and linkages 18. Referring to FIG. 4a, each blade has a cutting edge 34, a shearing surface 36 and a tissue contact surface or edge 38 that extends along the cutting edge and contacts the tissue 40 as the blades close.

The inner blade element 24 is preferably metal, such as stainless steel, or other suitable material that is of high strength and will hold a sharp cutting edge for repeated use. As best seen in FIGS. 4–7, the inside surface of the inner blade element 24 forms the cutting edge 34 and shearing surface 36 of each blade. A forward surface 42 of the inner blade element extends along the cutting edge and the tissue contact surface for substantially the entire length of the blade segment 30.

Insulative material 26, separates the inner blade element 24 from the outer blade element 28. The insulative material may be made any suitable material that has sufficient resistance to electrically insulate the inner and outer blade elements. Preferably, the insulative material 26 also has sufficient bonding strength for bonding together the inner and outer blade elements. Because the outer blade element 28 does not include the shearing surface or cutting edge, the forces exerted on the outer blade element are limited, and the bond does not have to be as strong, for example, as employed in U.S. Pat. No. 5,352,222. It is believed that a relatively thin layer or film of insulation, such as the thickness of ordinary electrical tape, will provide sufficient insulation between the inner and outer blade elements. The spacing between inner and outer blade elements at the tissue contact surface is preferably between about 0.002 and 0.050 inches. Ordinary adhesives or materials that are suitable for bonding to metal in medical applications should suffice for bonding the inner and outer blade elements together. Alternatively, epoxy material, such as AF125 by 3M Company, as described in detail in U.S. Pat. No. 5,352,222, may be used to provide the insulative layer.

Outer blade element 28 is preferably a thin metal plate or strip, such as stainless steel or aluminum. Forward edge 44 of outer blade element 28 extends along the tissue contact surface 38, generally parallel to and spaced from the forward surface 42 of the inner blade element 24. As shown in longitudinal cross-section in FIG. 3, the insulating material 26 and outer blade element 28 preferably extend along the entire length of blade segment 30, including around the distal-most end of the blade segment.

The scissors of the present invention are preferably intended for connection to a voltage source, such as to the bipolar terminals of a commercially available bipolar RF energy generator. The bipolar RF generator may be connected to the scissors of the present invention at connectors 46 and 48 located near handle 22. Connector 46 is attached to an insulated conductor 50 that extends through shaft 14 and is connected at the distal end to each of the outer blade elements 28 of each blade. The other connector 48 is in electrical contact with the actuator rod 20 and shaft 14 which, in turn, are in electrical contact with the inner blade elements 24 of each blade via linkage 18 and pivot pin 16, respectively. Accordingly, the inner blade elements of each blade are attached to the same terminal of the voltage source and therefore have the same polarity. A standard insulating material such as plastic shrink tubing acts as a covering 45 along the outside surface of shaft 14, and protects surrounding tissue by preventing inadvertent conduction of electricity to or from the surface of the shaft. Alternatively, the shaft could be made entirely of insulative material, and electrical communication to the outer blade elements could be solely through the actuator rod, or vice versa.

FIGS. 4–7 show various possible blade configurations, in cross-section, as the blades close on tissue to be severed. Referring first to FIG. 4, FIG. 4a depicts the blades as they are closed and when they first come in contact the tissue 40 to be severed. Each blade has a shearing surface 36 and cutting edge 34. Each blade also includes an inside or forward tissue contacting edge surface 38. The inner blade element 24 forms the cutting edge and shearing surface of each blade. The inner blade also includes the forward edge or surface 42 that extends along the cutting edge for essentially the entire cutting length of the blade. The outer surface and back edge of the inner blade element are covered by insulative material 26. The insulative material 26 also extends beyond the back edge of inner blade element 24 to form an overhanging lip 52 of insulative material. This overhanging lip has a width approximately the same as or slightly greater than the width of the forward edge 42 of the inner blade element.

Outer blade element 28 extends along the tissue contacting edge surface 38 of the blade for substantially the entire length of the blade segment 30, and, as seen in cross-section, overlies only a portion of the outside surface of the inner blade element 24.

As shown by the arrows in FIG. 4a, when the tissue contacting edge or surface 38 of each blade comes into contact with the tissue 40 to be cut, current is believed to flow through the tissue between the inner blade element 24 and the outer blade element 28 of each blade, and as the blades come into proximity with each other, current flows through the tissue between the outer blade element 28 and inner blade element 24 of opposite blades. The current flow at the initial point of contacting the tissue is believed to be substantially between the inner and outer blade elements of the same blade along the tissue contacting edge. As the blades begin to cut the tissue and the distance between the blades decreases, the current flow between opposite electrodes of opposite blades increases.

FIG. 4b shows the blades in a position where the tissue has been severed, and the blades are not fully closed. At that position, it is understood that current flows substantially between the inner and outer blade elements of the same blade along the tissue contacting edge or surface 38, and may also flow between the outer blade element 28 and the shearing surface 36 of the inner blade element 24 of the other blade. The extent of current flow through the tissue in this situation may vary depending on the tissue type, position, thickness, and the extent to which the tissue is under tension.

FIG. 4c shows the blades in a fully closed position. At that position, the overhanging lip 52 of insulative material covers the forward edge 42 of the inner blade element 24 of the facing blade, essentially fully enclosing and insulating the inner blade elements 24 from tissue contact, and preventing current flow therethrough.

Figure 5C:
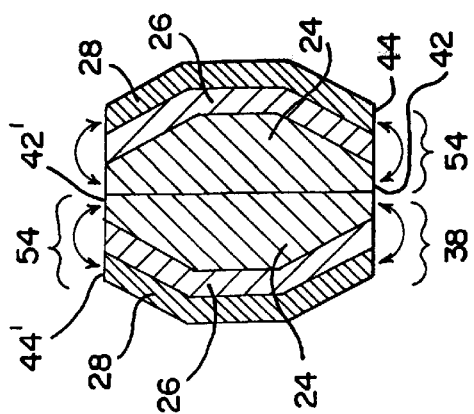
FIGS. 5a–5c are vertical cross-sectional views of another embodiment of scissor blades employing the present invention, showing the positions of the blades as they move from an open position in FIG. 5a in contact with the tissue to be cut, to an intermediate position in FIG. 5b just after the tissue is cut, and to a fully closed position in FIG. 5c.
Figure 5B:
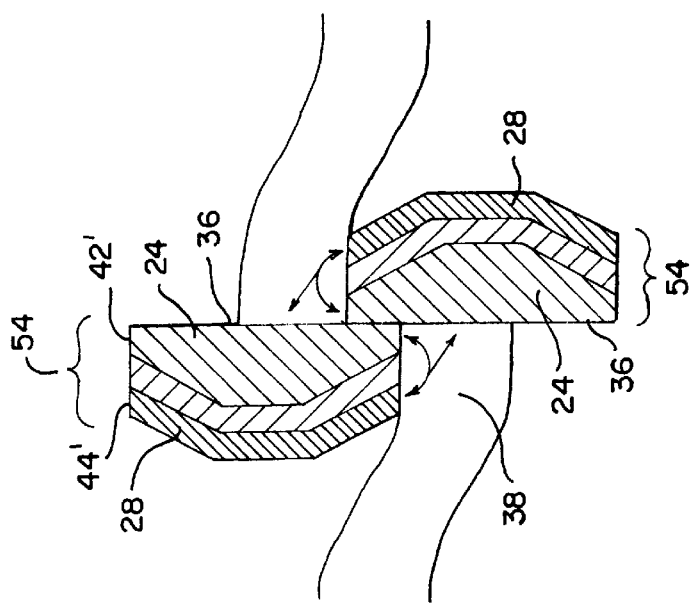
Figure 5A:
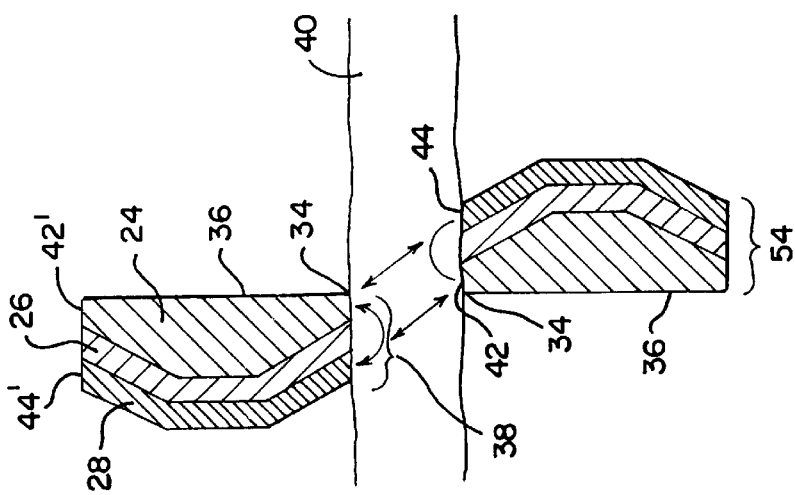

FIGS. 5a–5c show an alternative embodiment of the present invention in which each of the blades similarly has a cutting edge 34, shearing surface 36, and tissue contacting edge or surface 38 for contacting tissue as the blades close. In addition, in this embodiment each of the blades includes an rearward edge or surface 54, which is displaced from or opposite the tissue contacting edge or surface 38, and which may be used for cauterizing tissue in those situations where it is desirable to cauterize tissue with the rearward surfaces of the blades.

More specifically, as shown in FIG. 5a, each blade includes the inner blade element 24, insulative material 26 over only the outside surface of the inner blade element, and outer blade element 28 which fully overlies the outside surface of the inner blade element. With this construction, as the tissue contacting edge of each blade comes into contact with tissue 40 for cutting, current is understood to flow between the surfaces 42 and 44 of the inner and outer elements of the same blade, and between the inner blade surface 42 and the outer blade surface 44 of opposite blades. As the blades are moved to a closed position, as shown in FIG. 5b, current is believed to flow between the outer blade surface 44 and the inner blade surface 42 of the same blade and between the inner blade element and outer blade element of the opposite blades. When the blades are fully closed, as shown in FIG. 5c, the forward and rearward surfaces 38 and 54 of the inner and outer electrodes of each blade are exposed, and current may continue to flow between the electrodes of each blade, when they are in contact with tissue.

Figure 9C:
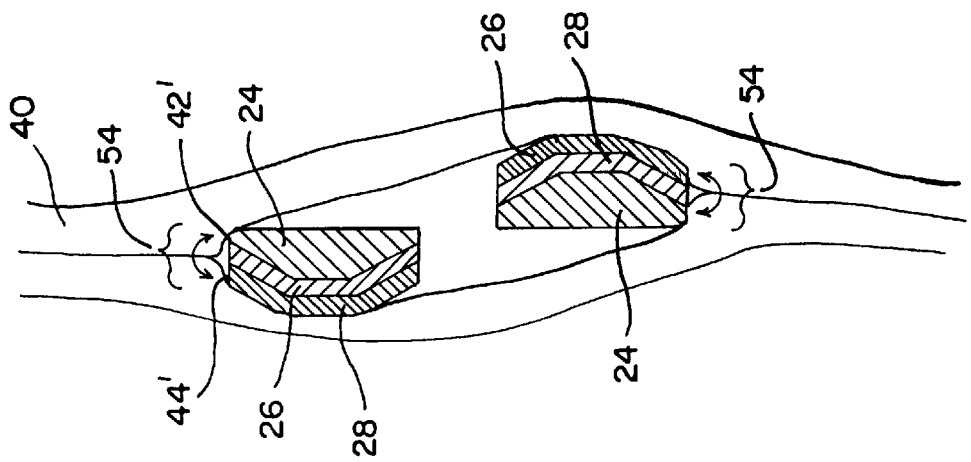
FIGS. 9a–9c are vertical cross-sectional views of the scissor blades of FIG. 5 showing the positions of the blades as they move from a closed position in FIG. 9a, to an intermediate position in FIG. 9b, to an open position in FIG. 9c, during a blunt dissection procedure.
Figure 9B:
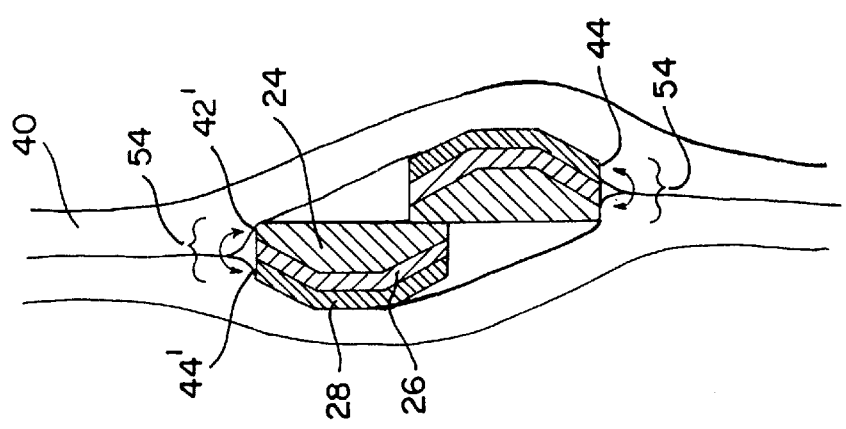
Figure 9A:
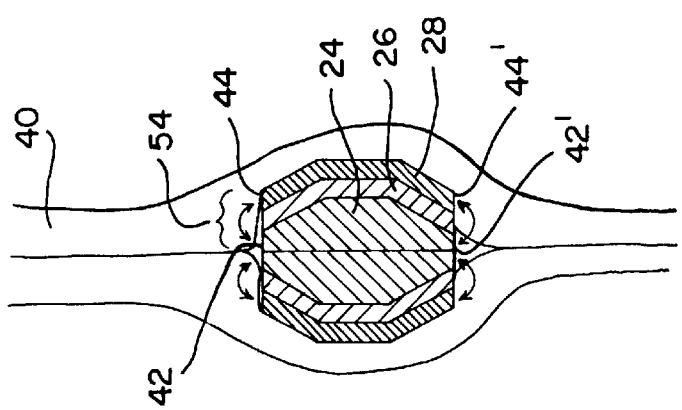

The rearward edge of each blade in FIG. 5 has the same construction as the inside or forward edge of the blade, with tissue contacting surfaces 42' and 44' extending along the rearward surface 54, and therefore may be used for assisting in severing and promoting hemostasis of tissue that is contacted by the outside of the blades in a procedure such as blunt dissection. FIGS. 9a–9c depict use of the scissors of FIG. 5 in a procedure such as a blunt dissection. A blunt dissection as depicted in FIG. 9 is where the scissors are inserted into the tissue in a closed or semiclosed position, and then opened to spread the tissue. Such a spreading action may result in bleeding from blood vessels ruptured during the procedure. In accordance with the present invention, the scissors of FIG. 5 may be used not only for promoting hemostasis during normal cutting but for promoting hemostasis during blunt dissection or the like.

FIG. 9a shows the scissor blades of FIG. 5 inserted into tissue 40 in a closed or near closed position. In this position, current flows through the tissue between surfaces 42 and 44 of the same blade at the inside tissue contacting surface and between surfaces 42' and 44' of the same blade at the rearward tissue contact surfaces. As the blades are moved to an intermediate position, the inside surfaces are no longer in close tissue contact and current flow between the inner and outer blade elements reduces or ceases. Current continues to flow through the tissue in contact with surfaces 42' and 44', promoting hemostasis in the tissue as the scissors spread. This current flow and hemostasis continues as the scissors fully open, as shown in FIG. 9c.

Figure 6C:
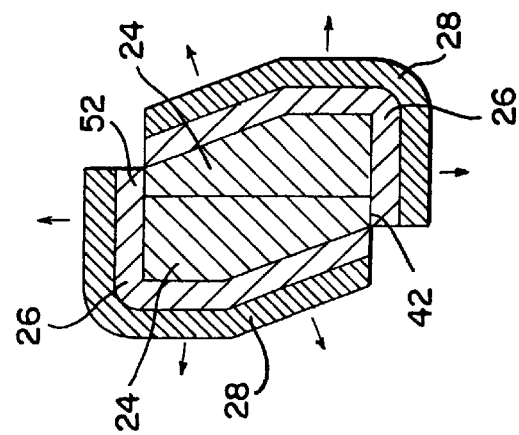
FIGS. 6a–6c are vertical cross-sectional views of a further embodiment of scissor blades employing the present invention, showing the positions of the blades as they move from an open position in FIG. 6a in contact with the tissue to be cut, to an intermediate position in FIG. 6b just after the tissue is cut, and to a fully closed position in FIG. 6c.
Figure 6B:
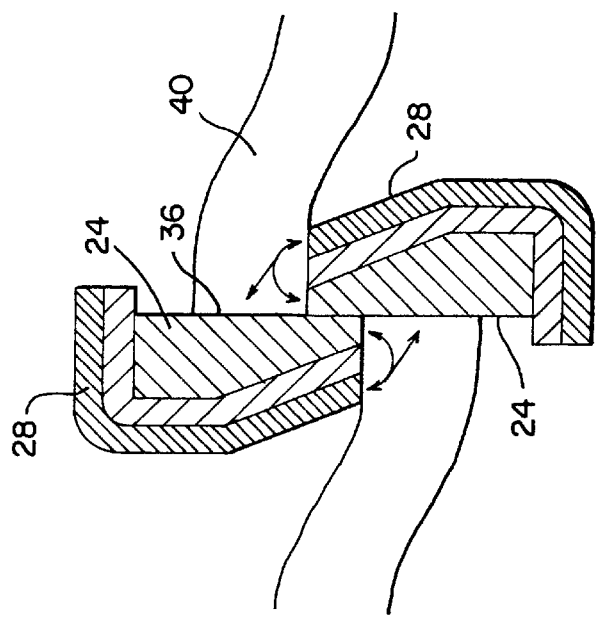
Figure 6A:
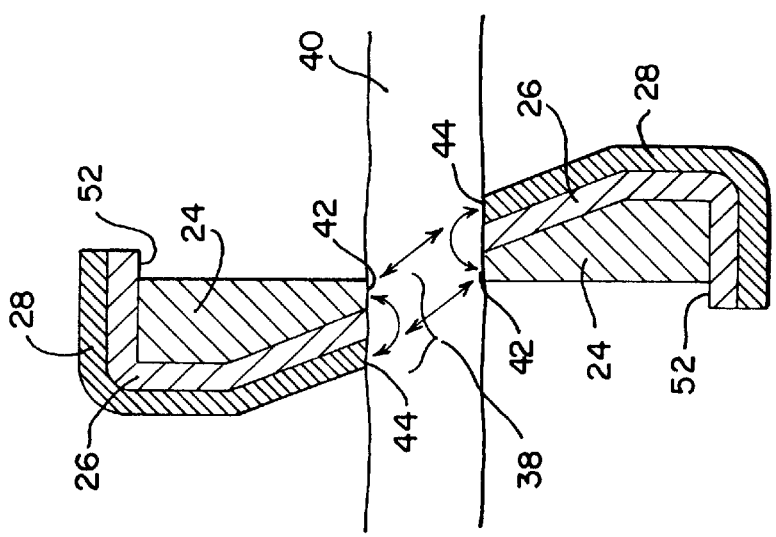

FIG. 6 shows another embodiment of the present invention, in which the inner blade element 24 is of essentially the same shape as that shown in FIG. 4, with the insulative layer 26 covering the same portion of the inner blade element as also shown in FIG. 4. In FIG. 6, however, the outer blade element 28 extends fully around the inner blade element to the same extent that the insulative material 26 extends around the material. The current flow between inner and outer elements of the blades in FIG. 6 is essentially the same as that described for FIG. 4. Also, similarly, when the blades are fully closed the inner blade elements 24 are essentially fully enclosed by the insulative material 26 and current flow between the inner and outer blade elements is effectively prevented. In this configuration, the outer electrode could be used as a monopolar electrode when the scissors are closed.

Figure 7C:
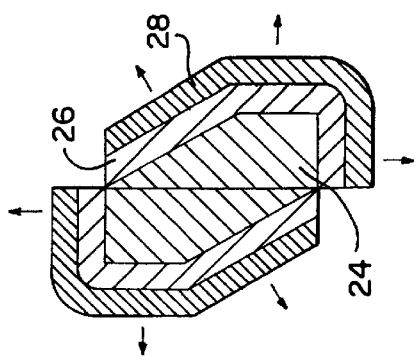
FIGS. 7a–7c are vertical cross-sectional views of a further embodiment of scissor blades employing the present invention, showing the positions of the blades as they move from an open position in FIG. 7a in contact with the tissue to be cut, to an intermediate position in FIG. 7b just after the tissue is cut, and to a fully closed position in FIG. 7c.
Figure 7B:
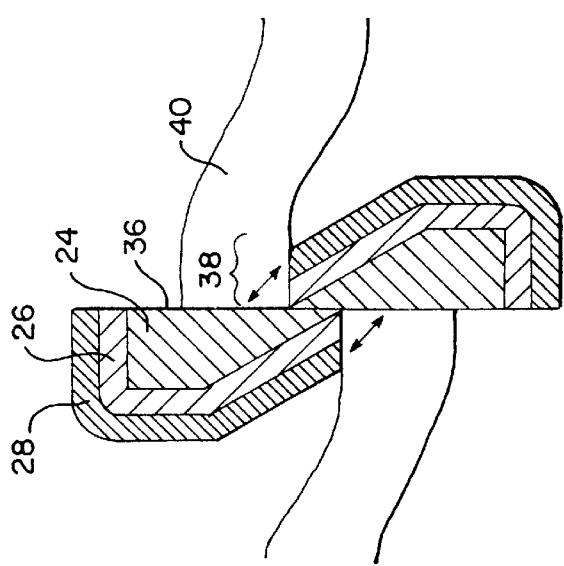
Figure 7A:
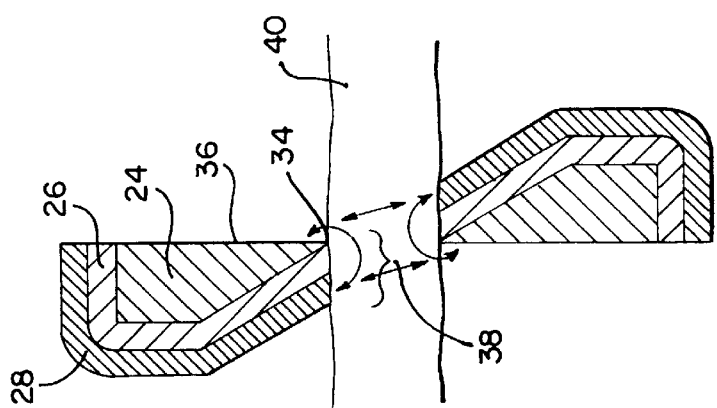

FIGS. 7a–7c show yet another embodiment of the present invention similar to that of FIG. 6. In this embodiment, however, the inner blade element 24 tapers to a point at the tissue contacting edge or surface. In this embodiment, it is believed that the maximum amount of current flow will occur between the outer blade element of one blade and the inner blade element of the other blade as the blades sever the tissue. It should be noted that the wider the inner blade element surface 42 is, the more current will flow between electrodes (inner and outer elements) of the same blade, and the narrower the surface 42, the more current will flow between electrodes (inner and outer elements) of opposite blades. If the surface 42 width exceeds the typical current path length for bipolar energy (i.e., is greater than about 0.050 inches in width) then most of the current flow will occur between electrodes (inner and outer elements) of the same blade.

Figure 8:
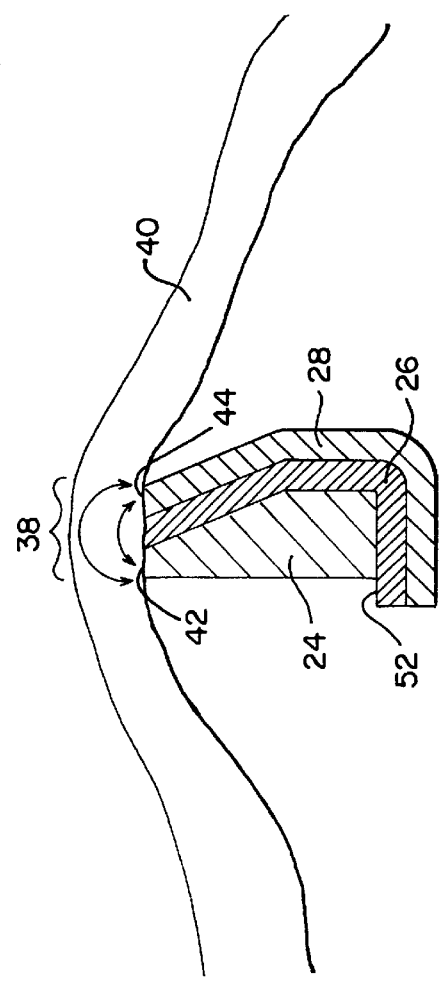
FIG. 8 is a vertical cross-sectional view of one of the scissor blades of FIG. 6, showing how a single blade may be used to promote hemostasis in tissue.

Finally, FIG. 8 depicts how the forward or tissue contact surface of a single blade embodying the present invention may be used to promote hemostasis independent of the tissue being severed.

Although FIGS. 4–7 depict various alternative constructions for the blades of the present invention, the present invention is not limited to these particular versions, and it is anticipated that other blade configurations may be used embodying the present invention which depart from the particular construction shown in FIGS. 4–7.

What is claimed is:

1. An electrosurgical instrument for cutting and coagulating tissue, comprising:
    (a) a pair of blades pivotally joined for relative movement in a scissors-like action between open and closed positions, each of said blades including a conductive blade member and a conductive electrode electrically isolated from the blade member, each blade member having a shearing surface, said shearing surfaces of said blade members being in face-to-face relationship;
    (b) means coupled to said pair of blades for effecting relative movement of said blades in said scissors-like action; and
    (c) means for applying a voltage across said conductive electrode and conductive blade member of each blade.

2. Tissue cutting apparatus comprising:
    a pair of blades joined for relative movement in a scissor-like action between open and closed positions;
    a handle operatively connected to at least one of said blades for effecting relative movement of said blades in a scissors-like action;
    each of said blades comprising a tissue contacting surface for contacting tissue, said contacting surface of each blade including first and second spaced apart electrodes extending along said surface, said electrodes being adapted for connection to a voltage source having a pair of terminals of opposite polarity whereby current flow between said first and second electrodes of each blade promotes hemostasis in tissue contacting said surface,
    said first electrode of each of said blades also defining a shearing surface and a cutting edge, said shearing surfaces of said blades being in face to face relationship, and both of said first electrodes being adapted for connection to the same terminal of the voltage source so that they are of like polarity.

3. Tissue cutting apparatus comprising:
    a pair of blades joined for relative movement in a scissor-like action between open and closed positions;
    a handle operatively connected to at least one of said blades for effecting relative movement of said blades in a scissors-like action;
    each of said blades comprising a tissue contacting surface for contacting tissue, said contacting surface of each blade including first and second spaced apart electrodes extending along said surface, said electrodes being adapted for connection to a voltage source having a pair of terminals of opposite polarity whereby current flow between said first and second electrodes of each blade promotes hemostasis in tissue contacting said surface,
    electrically insulative material disposed between said electrodes, and
    said electrically insulative material of said blades substantially enclosing said first electrode to prevent tissue contact with said first electrode when the blades are in a fully closed position.

4. Tissue cutting apparatus comprising:
    a pair of blades Joined for relative movement in a scissor-like action between open and closed positions;
    a handle operatively connected to at least one of said blades for effecting relative movement of said blades in a scissors-like action;
    each of said blades comprising a tissue contacting surface for contacting tissue, said contacting surface of each blade including first and second spaced apart electrodes extending along said surface, said electrodes being adapted for connection to a voltage source having a pair of terminals of opposite polarity whereby current flow between said first and second electrodes of each blade promotes hemostasis in tissue contacting said surface, said tissue contacting surface comprising a tissue contacting edge, and each of said pair of blades further comprises an edge displaced from said tissue contacting edge, said first and second electrodes extending along said tissue contacting edge and said displaced edge.

5. The tissue cutting apparatus of claim 4 wherein said displaced edge is located opposite said tissue contacting edge for contacting adjacent tissue, said tissue contacting edge being disposed for contacting tissue between said blades and said displaced edge being disposed for contacting tissue outside said blades.

6. Electrosurgical scissors comprising:

an elongated shaft having proximal and distal ends;

a pair of blades carried at said distal end of said shaft and joined for relative movement in a scissor-like action between open and closed positions;

a handle carried at the proximal end of said shaft and a link extending through said shaft and operably connected to said blades and said handle for movement of said blades between said open and closed positions;

each of said blades including first and second electrodes, said first electrode defining a shearing surface and a cutting edge, said second electrode extending generally parallel to said cutting edge and being spaced from said first electrode;

said shearing surfaces of said first electrodes for each of said blades being in face-to-face relation;

an insulated conductor extending along said shaft for connecting said second electrodes to a first terminal of a bipolar RF energy source; and said shaft or link being of conductive material for connecting said first electrodes to a second terminal of a bipolar RF energy source.

7. The electrosurgical scissors of claim 6, wherein said shaft includes an outer surface that is substantially of non-conductive material.

8. A method for dissecting tissue comprising:

providing tissue dissecting apparatus comprising a pair of blades joined for relative movement in a scissor-like fashion between open and closed positions, each of said blades comprising a rearward tissue contacting surface for contacting tissue as said blades are opened, the rearward tissue contacting surface of each blade comprising first and second electrodes extending along said contacting surface;

inserting the blades into tissue to be dissected;

applying a voltage between said first and second electrodes of each blade so that current passes between said first and second electrodes of each blade; and opening the blades to spread the tissue.

9. Tissue cutting apparatus comprising:

a pair of blades movable in a scissor-like action between open and closed positions, each of said blades including a shearing surface, said shearing surfaces of said blades being in face-to-face relationship;

a handle operatively connected to at least one of said blades for effecting relative movement of said blades in a scissors-like action;

each of said blades comprising a pair of electrodes connectable to opposite terminals of a bipolar RF energy source, said shearing surface of each blade comprising one of said electrodes of like polarity.

10. Electrosurgical scissors for attachment to a bipolar electrical energy source including two terminals, said scissors comprising:

(1) a pair of blades, each blade including:
  (a) a metal blade member comprising:
    (i) an inside-facing surface defining a cutting edge and shearing surface,
    (ii) an outside-facing surface, and
    (iii) a proximal extension for joining said blades;
  (b) a layer of insulation over said outside-facing surface;
  (c) a layer of conductive material over said layer of insulation; and
  (d) a handle operatively connected to at least one of said blades for effecting relative movement of said blades in a scissors-like action;

(2) said proximal extensions of said blade members being pivotally joined for movement of said blades in a scissor-like action;

(3) each of said metal blade members being connectable to one terminal of the bipolar electrical energy source, and (4) each of said layers of conductive material being connectable to the other terminal of the bipolar electrical energy source.

* * * * *